(12) United States Patent
Astudillo de la Vega (10) Patent No.: US 10,285,963 B2
(45) Date of Patent: May 14, 2019

(54) COMBINATION OF METABOLIC BIO-ENERGETIC AND NUTRA-EPIGENTIC REGULATORS, NUTRACEUTICAL COMPOUNDS IN CONVENTIONAL AND NANOTECHNOLOGIES COMBINATION TO REVERT AND PREVENT THE CHRONIC DAMAGE ACCELERATED CELLULAR SENESCENCE PRODUCED BY DIABETES AND OTHER DEGENERATIVE CHRONIC COMPLEX DISEASES

(71) Applicant: Horacio Astudillo de la Vega, Cuauhtémoc (MX)

(72) Inventor: Horacio Astudillo de la Vega, Cuauhtémoc (MX)

( * ) Notice: Subject to any disclaimer, the term of this patent is extended or adjusted under 35 U.S.C. 154(b) by 0 days.

(21) Appl. No.: 15/176,422

(22) Filed: Jun. 8, 2016

(65) Prior Publication Data

US 2016/0354331 A1    Dec. 8, 2016

Related U.S. Application Data

(60) Provisional application No. 62/172,339, filed on Jun. 8, 2015.

(51) Int. Cl.
| | |
|---|---|
| *A61K 31/198* | (2006.01) |
| *A61K 31/05* | (2006.01) |
| *A61K 47/02* | (2006.01) |
| *A61K 9/10* | (2006.01) |

(52) U.S. Cl.
CPC ............ *A61K 31/198* (2013.01); *A61K 31/05* (2013.01); *A61K 9/10* (2013.01); *A61K 47/02* (2013.01)

(58) Field of Classification Search
CPC .................................................. A61K 31/198
See application file for complete search history.

(56) References Cited

FOREIGN PATENT DOCUMENTS

EP    2163252 A1 *  3/2010    ............. A23D 9/007

OTHER PUBLICATIONS

John M Pezzuto, Tamara P Kondratyuk & Talysa Ogas (2013) Resveratrol derivatives: a patent review (2009-2012), Expert Opinion on Therapeutic Patents, 23:12, 1529-1546, DOI: 10.1517/13543776.2013.834888.*
Fan et. al., Bioorganic & Medicinal Chem. Letters, 1997, 7(24): 3107-3112.*
Egbuoni et el., American Journal of Biochemistry and Molecular Biology, 3(1):50-60, 2013.*
Elshorbagy et al., Obesity, (2012)20, 473-481.*
Villar et al., Metabolic Syndrome and Related Disorders, 12(10), 2014, Abstract.*

* cited by examiner

*Primary Examiner* — Svetlana M Ivanova
(74) *Attorney, Agent, or Firm* — Shumaker, Loop & Kendrick, LLP (57) ABSTRACT

The invention relates to compounds of natural origin and their pharmaceutically acceptable and active mixture to decrease glucose, cholesterol, uric acid, and body fat the high levels, cytoprotection of damaged organs, activation of metabolism and cell proliferation. It is exemplified with the pharmaceutical composition comprising a pharmaceutically effective amount of the compounds of Formulation I, and its method on in vitro and in vivo systems. Formulation I and its variables can be used to treat hyperglycemia, gout, dyslipidemia, obesity, insulin resistance, diabetes mellitus, diabetes insipidus, type 1 diabetes, type 2 diabetes, microvascular complications, macrovascular complications, lipid disorders, pre-diabetes, arrhythmias, myocardial infarction, renal and pancreatic complications, cardiovascular complications.

9 Claims, 10 Drawing Sheets

COMBINATION OF METABOLIC BIO-ENERGETIC AND NUTRA-EPIGENTIC REGULATORS, NUTRACEUTICAL COMPOUNDS IN CONVENTIONAL AND NANOTECHNOLOGIES COMBINATION TO REVERT AND PREVENT THE CHRONIC DAMAGE ACCELERATED CELLULAR SENESCENCE PRODUCED BY DIABETES AND OTHER DEGENERATIVE CHRONIC COMPLEX DISEASES

TECHNICAL FIELD

The present invention focuses on definition of pharmaceutical compositions and proposed method for the treatment of metabolic syndrome, diabetes mellitus and aging. Compounds and compositions of natural origin are disclosed in the description. More particularly, this invention relates to a method of treating diseases based on the use of responses developed in cellular systems and mammalian organisms (animals and humans) with the pharmaceutically acceptable doses of the compounds being part of Formulation I, such as metabolism control and cell growth.

BACKGROUND OF THE INVENTION

Metabolic syndrome, formerly known as syndrome X, is an intermediate state between normal metabolism and type 2 diabetes mellitus. It is an emerging epidemic that has been defined as a series of metabolic risk factors predisposing people to heart and coronary disease and chronic renal failure, among other disease states. Metabolic syndrome is associated with abdominal obesity, atherogenic dyslipidemia, hypertension, proinflammatory and prothrombotic state, with or without glucose impairment, i.e. diabetes. Symptoms are related to high triglyceride levels, low high density lipoprotein levels, increased blood pressure or hypertension and increased glucose levels, and inflammation symptoms. Each of these characteristics is a significant risk factor for development of vascular dysfunction and cardiovascular, renal and hepatic diseases (Eckel R. H et al in Lancet, 2005, 365: 1415) Metabolic syndrome increases the risk of premature death, therefore, effective and affordable strategies to help reduce cardiometabolic alteration factors and to control the syndrome are important goals to benefit a large population being under high risk.

Currently the main approaches to treat people with metabolic syndrome are aimed at reducing the underlying causes, treating hypertension and other cardiovascular risk factors, and control insulin resistance. Treatment of metabolic syndrome includes lifestyle changes, along with drug treatment. In addition to treating metabolic syndrome implementing dietary guidelines and adequate physical activity to address the many underlying mechanisms of metabolic syndrome, a series of medications designed to control the altered levels of metabolites associated with manifestation of the disease state have been developed, incorporating various biologically active nutritional compounds aimed at the same goal. Functional knowledge of nutrient impact, especially amino acids and polyphenols in diet on different molecular targets, makes possible to develop a composition of naturally occurring compounds to treat obesity, metabolic syndrome, diabetes and aging. Some concepts and patents related to the subject of the present invention are described below.

Lodder and Cassis (Lodder R A and Cassis L A in US Patent 2015/9060962 Jun. 23, 2015) patented pharmaceutical compositions comprising D-tagatose with or without stilbene or stilbenoid, or derivatives thereof, to prevent or treat atherosclerosis, metabolic syndrome, obesity or diabetes. Silbenoids such as resveratrol (3, 5, 4-trihydroxy-trans-stilbene) which is a type of natural phenol and a phytoalexin produced in plants was applied during the response to pathogen attack or other injury. Large amounts of resveratrol can be found in different types of berries, grapes, cranberries, etc. (Fremont in Life Sci, 2000, 66: 663). Prior to that patent, Baur et al. (J. A. Baur et al in Nature, 2006, 444 (7117). 337) and Do et al. (Do G M et al in Biochem Biophys Res Commun, 2008, 374 (1). 55) reported the effect of resveratrol to improve health and survival of mice on diets high in calories, control alterations in cholesterol levels, among other capabilities. Another compound chemically related to resveratrol, pterostilbene known as 3,5-dimethoxy-4'hydroxystilbene, is characterized by displaying similar effects to resveratrol.

Sirtuins are enzymes with histone deacetylase and some transcription factor activity that regulate metabolic pathways involved in development of cardiovascular diseases, aging and stress resistance (Jiang W J Biochem. Biophys. Res. Commun., 2008, 373 (3): 341). It is considered that resveratrol directly or indirectly activates SIRT1 (NAD-dependent sirtuin-1 deacetylase) and PGC-1 (gamma receptor coactivator activated by peroxisome proliferator), and affects functioning of mitochondria (Lagouge M. et al in Cells, 2006, 127 (6): 1109; Alcain F J and Villalba J M in Expert Opin Ther Pat, 2009, 19 (4): 403; Beher D. et al in Chem Biol Drug Des, 2009, 74 (6): 619). In cells treated with resveratrol, there is an increase in SOD2 (MnSOD) action (superoxide dismutase 2, mitochondrial, also known as manganese-dependent superoxide dismutase) reducing superoxide, which involves resistance to mitochondrial dysfunction, permeability transition, and death by apoptosis in several diseases. It has been found that resveratrol also acts as a GPER agonist (GPR30) (G protein-coupled estrogen receptor 1, also known as G protein-coupled receptor 30) (Prossnitz E. R. and Barton M. in Mol. Cell. Endocrin. 2014, 389 (1-2): 71). A possible action mechanism of resveratrol can be attributed to autophagy modulation (autophagocytosis—aimed at eliminating dysfunctional mechanism components) (Ghosh H. S. et al in PLoS ONE, 2010, 5 (2). e9199). Laboratory animals have shown the positive effects of resveratrol as an antidiabetic treatment (Baur J A et al in Nature, 2006, 444 (7117): 337; Lagouge M. et al in Cells, 2006, 127 (6). 1109.). This compound acts as PPAR gamma agonist (gamma receptor activated by peroxisome proliferator (PPAR-γ or PPARG), also known as glitazone receptor, or R1C3 (nuclear receptor subfamily 1, group C, member 3) is a type II nuclear receptor), considered as a pharmacological target for treatment of type 2 diabetes (L. Wang et al in Biochem Pharmacol 2014, 92 (1): 73). Peroxisomes are organelles that may cause disease and aging processes while not properly functioning. The ability to stimulate the activity of endothelial nitric oxide synthase (eNOS) and inhibit platelet aggregation is attributed to resveratrol (Vita J. A. Duffy S J in Curr Opinion Lipid, 2003, 14 (1). 21; Olas B. and. Wachowicz B. in Platelets, 2005, 16 (5): 251).

Plant extracts may be considered as antioxidant source, resveratrol analogs. US Patent 2016/9,278,104, Mar. 8, 2016 for Romero T., established the use of Nelumbo nucifera leaf extract to reduce and/or eliminate one or more risk factors associated with metabolic syndrome. The composition considers the presence of creatinine—a nitrogenated organic acid much like amino acid structure located in muscles and nerve cells of different living organism. It is synthesized naturally in the liver, pancreas and kidneys from amino acids such as arginine, glycine and methionine at a rate of one gram of creatine per day. It is considered as an immediate and direct vector to transport ATP and supply energy to muscle myofibrils.

Gokaraju G. R. et al., in US Patent 2016/9,241,964, Jan. 26, 2016 establishes the composition of phytochemical fractions for pharmaceutical use or as a dietary supplement derived from *Sphaeranthus indicus* and/or *Garcinia mangostana*. The composition is applied for obesity, metabolic syndrome, diabetes and other metabolic disorder control, prevention and treatment, and also to regulate energy expenditure, prevention of coronary artery and abdominal aorta atherosclerotic plaques, increase insulin sensitivity, control of glucose levels, triglyceride levels and balance glucose levels in mammals. Extracts which contain amino acids among other components are mentioned; however, those are not disclosed.

It is widely known that amino acids are an important part in the synthesis of various proteins involved in human metabolism. This invention is considered to be the reason for which the composition can be selected for the treatment and prevention of metabolic syndrome, obesity, diabetes, and aging.

Varfolomeev S. D. and Gurevich K. G. (in *Russian Chemical Bulletin,* 2001, 50 (10): 1709) performed biocomputer analysis demonstrating that glycine amino acid is most frequently found (37.5%) in defined positions of primary sequences in different enzyme families. Authors attribute this property to the role of glycine in enzyme architecture: being an amino acid with the chiral atom which allows movement and flexibility to protein chains. This demonstrates the importance of glycine for metabolism. The following 5 amino acids are aspartic acid (12.9%), cysteine (6.7%), histidine (6.2%) and arginine (5.5%). Cysteine is responsible for maintaining the conformation of various proteins due to the formation of sulfur bridges. Histidine and arginine like aspartic acid are common in enzyme active sites by playing a role in the catalytic site as core agents and electrophiles.

In the case of arginine (Wu G. A. B. et al in *Curr Opin Clin Nutr Metabol Care,* 2000, 3 (1): 59) its ability to help reduce insulin resistance is reported, allowing a decrease in the amount of insulin in diabetes treatments, increase glucose tolerance and improve insulin sensitivity in type 2 diabetes mellitus.

Cysteine is the limiting substrate for glutathione synthesis—responsible for protecting cells against viruses, bacteria, fungi, carcinogens, as well as against other disease states. Oral cysteine applied without any other components is not recommended because it is rapidly catabolized to the gastrointestinal tract passing to a toxic state. Cysteine has antioxidant properties, due to the ability of thiols to participate in redox reactions. These cysteine antioxidant properties are mostly expressed in tripeptide glutathione. Availability of oral glutathione is insufficient, thus it must be biosynthesized from the amino acids that constitute it—cysteine, glycine and glutamic acid, from which cysteine is the limiting substrate. Different trials supplemented by laboratory tests have shown that aging is directly associated with a progressive decrease in plasma cysteine and glutathione intracellular concentration. This decrease leads to age-related oxidative stress. Cysteine supplementation above normal diet reduces the various aging processes by helping the bone and muscular systems, reducing inflammation and levels of cytokines (L. Wang et al. In *Biochem. Pharmacol.* 2014, 92 (1): 73).

Control of cellular proliferation is essential to the proper functioning of any organism. Alteration of this regulation is the cause of diseases such as cancer—with unlimited and uncontrolled cell proliferation due to genetic mutations. Conversely a loss of the ability of cell proliferation is one of the factors causing aging.

Extracellular control of cell division may be performed by cell cycle mitogens, several growth factors as well as by survival factors. Mitogens are proteins that stimulate cell division, counteracting intracellular stop mechanisms (Rb) that block cycle progression.

The growth of any organism or organ depends on both growth and cell division. If cells should be divided without growing, they would become smaller each time. Growth factors stimulate cell growth (cell mass increase) by promoting synthesis and inhibition of proteins and other macromolecules. Cell growth does not depend on cell cycle. For example, nerve and muscle cells grow especially after cell division. Like most mitogens, growth factors bind to cell surface receptors which then activate different intracellular signaling pathways, which may induce: increased protein synthesis or a decreased protein degradation. All this will lead to cell growth.

Survival factors promote cell survival by suppressing intracellular death programs or apoptosis. These signal need from other cells for survival help cells survive only when and where required. Neurons for example, are produced in excess and they compete each other in obtaining growth factors and those with the largest amount will survive. As mitogens and growth factors, survival factors tend to bind to cell membrane receptors which activate intracellular signaling pathways that inhibit cell death, usually by regulating proteins belonging to the Bcl-2 family. Some survival factors are IL-3, SCF, IGF-1, which are mainly secreted by the liver in response to signals from growth hormone (GH).

Based on the above and for the purpose of solving above mentioned problems, the object of present invention is to provide the use of a formulation consisting of: resveratrol, glycine, arginine and cysteine, setting the range of component concentrations based on the study of *Artemia salina* model. What is patented in this case is the use of the formulation, and the method of its application for treatment of diseases. The formulation has the novel effect to stimulate proliferation of cell cultures and lymphocytes in vitro, without genotoxicity evidence, revealing the ability to decrease formation of visceral fat observed in healthy laboratory animals induced to diabetes, controllability of glycemia index with less insulin or without insuline shown in the model of alloxan-induced diabetes, cytoprotective effect of treatment presented in the pancreas of animals treated with alloxan, correction of symptoms of metabolic syndrome and obesity in patients treated during a 6-month period. In the examples described below it is demonstrated that the formulation has a revitalizing ingredient that act at the level of energy production, restoration of oxygen metabolism and reactivation of various enzymatic cycles related to sugar, fatty acid and cholesterol metabolism, increasing the energy available in the cells for increased functionality and vitality expressed in terms of increased proliferation. Examples demonstrate that when said formulation is applied in animals and humans, altered functions related to negative factors of diabetes, obesity and/or metabolic syndrome are normalized. According to these examples, treatment with the designed formulation is a method to control aging, metabolic syndrome, obesity and diabetes.

BRIEF DESCRIPTION OF THE DRAWINGS

FIG. 9. Comparison of histological changes observed at pancreas level in rabbits with induced diabetes, treated and untreated with Formulation I and insulin. Above, —Histological section of tissue removed from female pancreas treated only with insulin, complete destruction of the organ demonstrated: only adipose tissue with congested blood vessels and two lymph nodes with reactive changes were found, deliberate search was performed without identifying feasible pancreatic tissue. Below,—Histological section (10×) of female pancreatic tissue treated only with Formulation I (left), identifying the excretory portion pancreas preservation acini without histologic changes associated, however, endocrine component is not identified (islet cells); Image (40×) corresponds to an approach to integrating pancreatic excretory portion (acini) (right).

FIG. 10. Comparison of histological changes observed at kidney level in induced-diabetes rabbits treated and untreated with Formulation I and insulin. Above—Histological section of renal tissue of treated female only with insulin: at glomerular level with mesangial cell increase without atypia, focal thickening of blood vessel wall without formation of sclerotic nodules, which corresponds to early diabetic nephropathy characterized by mesangial slight increase (left); male kidney cut treated only with insulin, with good preservation of the bone cortex, abundant glomeruli with good cellularity with slight congestion, no sclerosis changes. In the tubular component there are changes by coagulative necrosis and nuclei pyknosis (right). In the middle—Histological female kidney cut treated with insulin and Formulation I to 90 mg/kg, showing good bone cortex conservation, identifying abundant glomeruli with good cellularity with very slight congestion, no sclerosis changes.

In the tubular component initial changes are seen by coagulative necrosis and pyknosis nuclei. Below,—histological section of male congestive kidney tissue under treatment with Formulation I to 70 mg/kg (left,—10×) with erythrocyte extravasation (microscopic bleeding) at medulla and cortex, identifying structures showing increased glomerular mesangial cells without atypia, slight congestion; drawing corresponds to an approach of congestive glomeruli (right—at 40×).

DETAILED DESCRIPTION OF THE INVENTION

Characteristic details of the invention consist of defining Formulation I, defining its application, biological effects in living systems at different levels (cellular, healthy animals or diabetes-induced, human organism). The following paragraphs describe the purpose of defining the invention, illustrate the novelty and utility of present invention, but without limiting the scope thereof and not intended to unduly limit it. The following examples are based on tests conducted to define Formulation I, as well as test their effects on in vitro and in vivo systems.

Description of the formulation comprising the basic compositions and preparation in the light of the invention, according to present invention is shown in Table 1.

TABLE 1

FORMULATION I

| Dose Size | 5 g-17 g |
| Dose per bag | 1 bag |
| Bags per box | 90 |

| Component | Dose-Range (Min-Max) | Purity (%) |
| --- | --- | --- |
| Glycine* | 3,000-7,000 mg | 98.5-101.5% |
| L-Arginine HCl* | 300-5,000 mg | 98.5% |
| L-Cysteine HCl* | 200-2,500 mg | 98.5-101.5% |
| Resveratrol* | 100-2,500 mg | 98% |

*Daily values in diet are not established
Approximate amounts for a 70 kg weight individual The composition according to claim 1 further characterized in that comprises one of the embodiments of the potential combinations of compounds of present invention with higher therapeutic effect for advanced disease cases, as well as integrating an embodiment of nanoparticles decreasing the dosage regime.

TABLE 2

| Dose Size | 6 g-19 g |
| Dose per bag | 1 bag |
| Bags per box | 90 |

| Component | Dose-Range (Min-Max) | Purity (%) |
| --- | --- | --- |
| L-Glycine* | 3,000-7,000 mg | 98.5-101.5% |
| L-Arginine HCl* | 2,000-5,000 mg | 98.5% |
| L-Cysteine HCl* | 1,000-2,500 mg | 98.5-101.5% |
| L_Methionine* | 500-1,500 mg (500 mg in nanoparticles) | 98.5-101.5% |
| Vitamin B6 (Pyridoxin-HCl) | 500-1,500 mg | 98.5-101.5% |
| Resveratrol* | 500-1,500 mg (500 mg in nanoparticles) | 98% |

*Daily values in diet are not established
**20 mg is 100% of daily requirement

Table 2 (above) shows a second formulation according to the disclosures herein.

Example 1

The assay was performed to evaluate the toxicity of components proposed for Formulation I (resveratrol, glycine, arginine and cysteine), on *Artemia salina* nauplii. *Artemia salina* is a crustacean sensitive to a wide range of compounds with biological activity and very different chemical structures. Michael et al. (Michael A. S. et al in *Science*, 1956, 123: 464) and Vanhaecke et al. (Vanhaecke et al in *Ecotoxicol Environ Saf* 1981, 5:382) proposed its use for toxicity testing. It is a test that allows conducting practically and economically toxicity studies of different nature substances. There has been very good correlation with other specific cytotoxicity tests. This model is accepted by the FDA (Food Drug Administration) and EPA (Environmental Protection Agency in 2002), as a test for evaluating the toxicity and ecotoxicity of pharmaceutical and/or food products.

The assay was performed according to the method standardized using different dilutions of each of Formulation I components. In an *Artemia salina* hatcher, 0.5 g cysts of *Artemia salina* were hatched in artificial seawater at 37 g/L at a temperature of 27° C. with constant aeration for 24 h. In every 5 wells out of a 96-well plate, 0.1 mL of artificial seawater (37 g/L) was applied with a single-channel pipette with ten nauplii, separated from the hatcher and counted one by one to achieve an exact separation of 10 nauplii. From a 2000 ppm stock solution of resveratrol, glycine, arginine and cysteine serial dilutions were made. Using a multichannel micropipette, 0.1 mL of the solutions prepared in the plate were added, achieving a final concentration of 62.5, 125, 250, 500 and 1000 ppm per five wells of nauplii. For blank samples, 10 untreated nauplii were placed in a 0.2 mL volume of artificial seawater (37 g/L). The microplate was incubated at 25° C. for 24 h. After incubation period, *A. salina* nauplii alive and dead were counted with a stereoscopic microscope and % mortality was determined. Toxicity was expressed as percent mortality of *A. salina* nauplii: 0-10% non-toxic, moderately toxic 11-50%, 51-90% highly toxic and 100% extremely toxic, considering the Gualdron et al, scale. (Gualdron R. et al in *Chem Rev. Col. Farm*, 1997, 26: 15 to 19). Component solutions of Formulation I were 5-fold tested. Data were analyzed with the Statistical Package Graph Pad Prism version 6, by analysis of variance (ANOVA) test and Tukey multiple comparisons ($p<0.05$).

Figure 1:
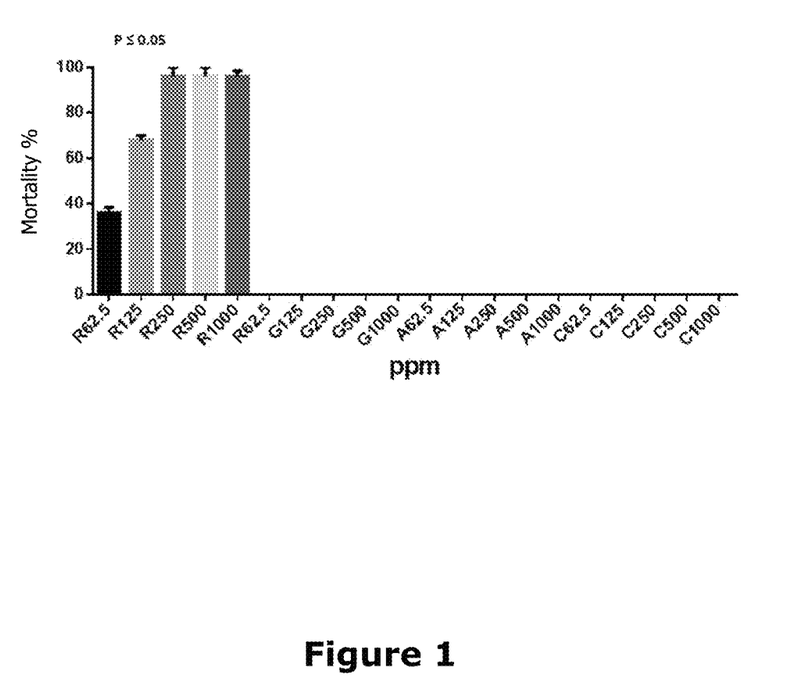
FIG. 1. Toxicity expressed in terms of mortality of *A. salina*, shown by resveratrol (R), glycine (G), arginine (A) and cysteine (C) components applied at different concentrations.

The results of data analysis were expressed as the ±standard deviation average and are presented in FIG. 1. Glycine, arginine and cysteine are toxicity free at any of the tested concentrations, thus suggesting that if toxicity may occur, it can only be just above 1000 ppm (FIG. 1). For resveratrol, in the 62.6 ppm solution a 38% mortality (moderate toxicity) was present, while LC50 (lethal concentration to 50% nauplii) was estimated as 89.48 ppm, suggesting that from this concentration resveratrol is highly toxic. This data is taken into account to define Formulation I: resveratrol concentration was selected below CL50; in the case of amino acids any concentration below 1000 ppm may be used.

Example 2

As Formulation I exemplified herein the following composition of the biologically active components is considered: 5.7 mg of resveratrol, 74.3 mg glycine, 5.7 mg arginine and 2.9 mg of cysteine/weight kg or solvent kg, for use in mammals (including humans) or cell cultures, respectively. The resveratrol concentration was selected considering the results defined in Example 1, i.e., about 15 times less than its $CL_{50}$ to prevent the toxicity manifestation. Arginine weight was taken equivalent to resveratrol, cysteine approximately 2 times less than resveratrol, and glycine as 13 times weight of resveratrol. Formulation I is an example of the mixture of biologically active components, which should not limit the scope of the invention. The Formulation I dose of 88.6 mg/kg is defined in this case.

Figure 2:
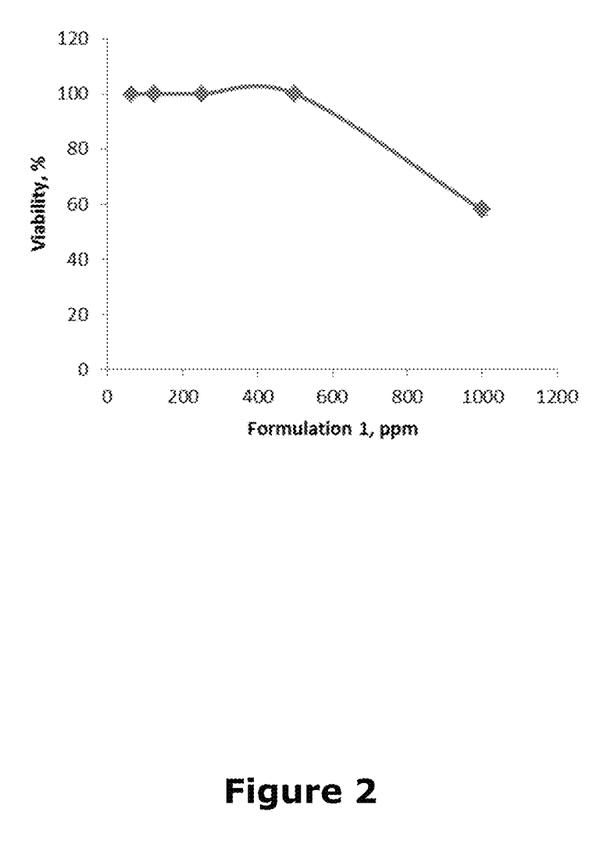
FIG. 2. *A. salina* viability in the presence of different concentrations of Formulation I.

Using Formulation I the assay similar to that described in Example 1 was performed to define the range of toxicity thereof. Results are presented in FIG. 2. It is shown that at a concentration lower or equal to 500 ppm, 100% of *A. salina* nauplii are kept alive and to 1000 ppm of Formulation I only 58% are alive. This indicates that according to model applied Formulation I is not toxic to a concentration up to 500 ppm, but at higher concentrations up to 1000 ppm a moderately toxic behavior is shown. This demonstrates that by using Formulation I, the concentration thereof may be varied in a wide range of concentrations and doses considering the absence of toxicity.

Example 3

Formulation I was applied to a test to determine their effects on human cells, i.e. to stimulate growth effects (mitogenic effect) or cause cell death (cytotoxic effect).

For the assay, a biological in vitro system using mononuclear cells culture from peripheral blood mononuclear cells—peripheral human lymphocytes was used. The system was selected because they form from 25 to 35% of leukocytes and they are the main immune response promoting cells since they recognize foreign antigens and activate cellular immune response mediators, causing proliferation or suppression phenomena before endogenous or exogenous stimuli. These cultures are widely used in research to evaluate the effects of various compounds (Marti-Centelles R. et al in *J. Med Chem Eur*, 2015, 103: 488). The effects on cell proliferation were assessed and $LC_{50}$ and $LC_{100}$ (concentrations that decrease the amount of living cells at 50 and 100%, respectively) of Formulation I on human lymphocytes in vitro were determined. As a positive control the test with concanavalin A (Con A) was performed, which is a globular plant-origin protein that induces mitosis in lymphocytes causing clonal proliferation (Ganem and Martin Gonzalez Baez F A O. in *Universo Diagnóstico*, 2000, 1 (1):1). Assay with RPMI-1640 (medium without treatment) was performed as blank. The effect of Formulation I, applied in a concentration range from 200 to 2000 ppm, was assessed by counting total number of cells and dead cells stained with trypan blue dye.

1 L of RPMI-1640 medium culture (SIGMA) was prepared supplemented with 10% FBS, adding 1 ml of 1× solution streptomycin and amphotericin B (SIGMA), sterilized through sterile filtration units (Corning) using 0.22 micron membranes. Serial dilutions from a stock solution of 2000 ppm of Formulation I at 200, 400, 600, 800, 1000 and 2000 ppm were prepared.

30 mL of peripheral blood from healthy volunteer donors by venipuncture were obtained, which was collected in plastic tubes containing EDTA as an anticoagulant. Then, mononuclear cells from peripheral blood (PBMC) isolated by a Ficoll-Hypaque density gradient (Sigma-Aldrich) by centrifugation at 1200 revolutions per minute (rpm) for 30 minutes at 25° C. were obtained. PBMC were washed twice with PBS 1×, cell pellet finally was resuspended in culture medium. PBMCs consist of monocytes and lymphocytes. Monocytic cells are characterized by being adherent cells which lack proliferative potential. Otherwise they represent the lymphocytes, which are cells in suspension, able to proliferate after an endogenous or exogenous stimulus. To separate monocytes from lymphocytes, obtained PBMC were horizontally cultured in 25 cm$^3$ boxes so that monocytes adhere to the surface over a period of 5 hours at 37° C. with humidified atmosphere, in a 5% $CO_2$ atmosphere. After incubation time, lymphocytes—the cells remaining in suspension were separated in sterile 1.5 ml tubes and centrifuged at 1200 rpm for 10 minutes (Eppendorf Centrifuge 5810-R), then 1 mL of culture medium was added to cellular package. A suspension of 500,000 cells/mL was prepared in Eppendorf tubes, to which were added different concentrations of Formulation I (200, 400, 600, 800, 1000 and 2000 ppm) adding a 1.25 mg/mL positive control of concanavalin A—an inducer of cell proliferation and blank—untreated cells, the culture medium was added. The samples were incubated at 37° C. in humidified atmosphere with 5% $CO_2$ for 48 hours, sufficient for lymphocytes to complete cell division showing a similar positive control proliferation (Con A) by the product or causing cellular toxicity otherwise. Upon terminating incubation, Eppendorf tubes which contained the different samples were centrifuged at 1200 rpm for 10 minutes, the supernatant decanted, and the cell pack was resuspended in 1 mL of RPMI-1640.

Optical light microscope with 40× objective was used. Cells were counted with Neubauer chamber using 0.05 mL suspension of each resuspended samples in 0.4 mL of PBS 1× and 0.05 mL of trypan blue. The assay was performed in triplicate in three independent events. The results were analyzed by the variance analysis test (ANOVA) with SPSS version 16 and then Dunnet's test was applied to discern whether a difference between control and experimental treatments was present, taking values of $p<0.05$ as significant.

Figure 3:
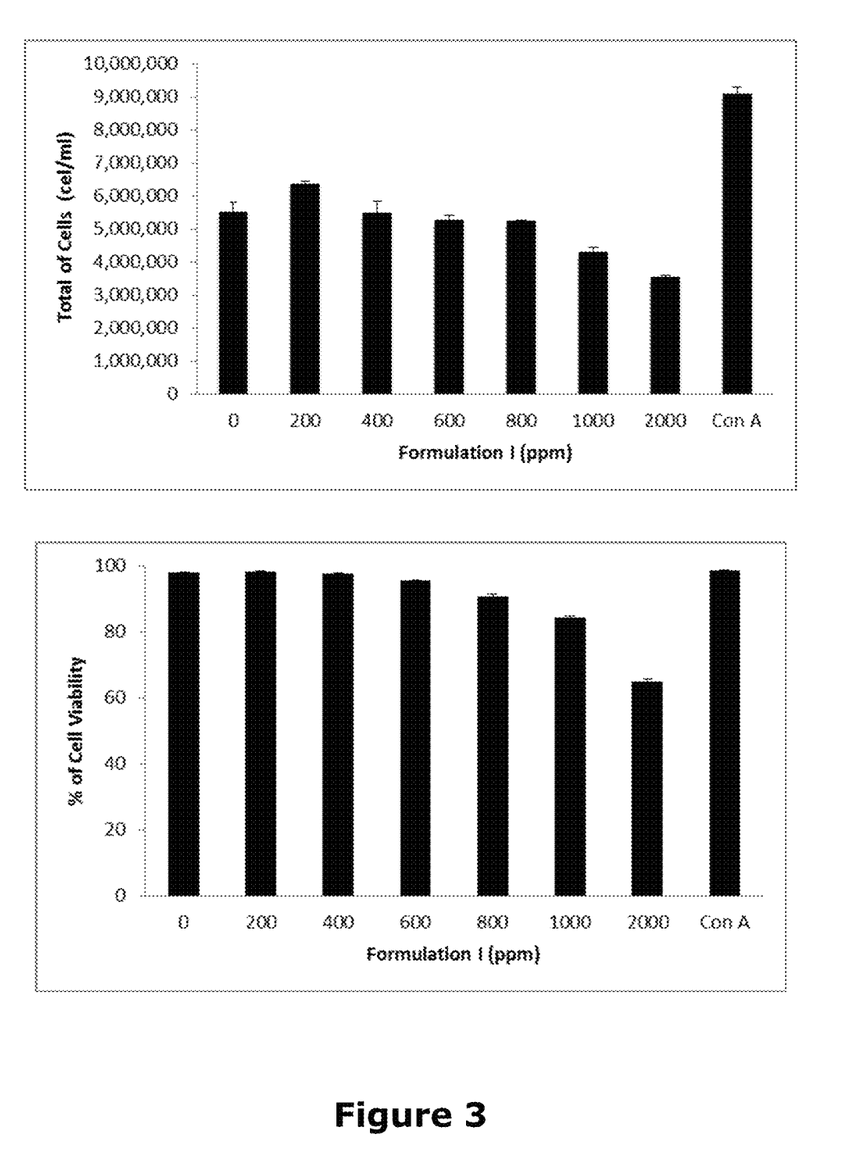
FIG. 3. Number of lymphocytes (top) and their viability (bottom) in samples treated with Formulation I at different concentrations.

FIG. 3 shows the test results. The effect of Formulation I applied to 200 ppm to increase the concentration of cells is apparent (number of cells per milliliter) to 15% significantly ($p<0.05$) when compared to the blank untreated: 6,372,333 and 5,518,333 cel/mL, respectively. As concanavalin A which counted an increase in the number of cells to 65% to obtain 9,101,667 cells/mL (FIG. 3) confirming its mitogenic activity. On the other hand, in the presence of concentrations of 1000 and 2000 ppm of Formulation I a decrease in cell number: 4,291,667 and 3,540,333 cells/mL, respectively was observed.

The percentages of relative cell viability (VCR) were calculated and found that in the presence of concentrations of 200, 400 and 600 ppm, 97% of the cells were alive as in Blank and positive controls. From 800 ppm, as well as 1000 and 2000 ppm of Formulation I cell viability of human lymphocytes significantly decreased (FIG. 3 below), with the following percentages of 90.58%, 84.38% and 64.96%, respectively. $LC_{50}$ and $LC_{100}$ for Formulation I were estimated at 2,726.8 ppm and 5,165.82 ppm, respectively. This value is significantly higher to that detected in the test with *A. salina* and proves that Formulation I lacks cytotoxicity at the applied doses. At doses of 50-90 ppm Formulation I is not cytotoxic according to both tests. These doses are in the range of stimulating lymphocyte proliferation confirming its important effect for the method of aging treatment.

Example 4

The following example shows that the proliferative effect and inhibitory effect shown in Example 3 are not related to the level of DNA (deoxyribonucleic acid) damage. For this purpose the comet assay, a rapid, sensitive, simple and quantifiable method to measure the degree of damage at the level of deoxyribonucleic acid (DNA) was developed. This assay is accepted as a tool to investigate compounds or deleterious effects on DNA repair (Azqueta A. and A. R. *Arch Toxicol Collins*, 2013, 87: 949). It is used in systems in vivo, in vitro, ex vivo in different scientific disciplines for genotoxicity tests, preclinical and clinical studies, ecotoxicology genetic testing, cytogenetics, photogenotoxicity, and the like.

Figure 4:
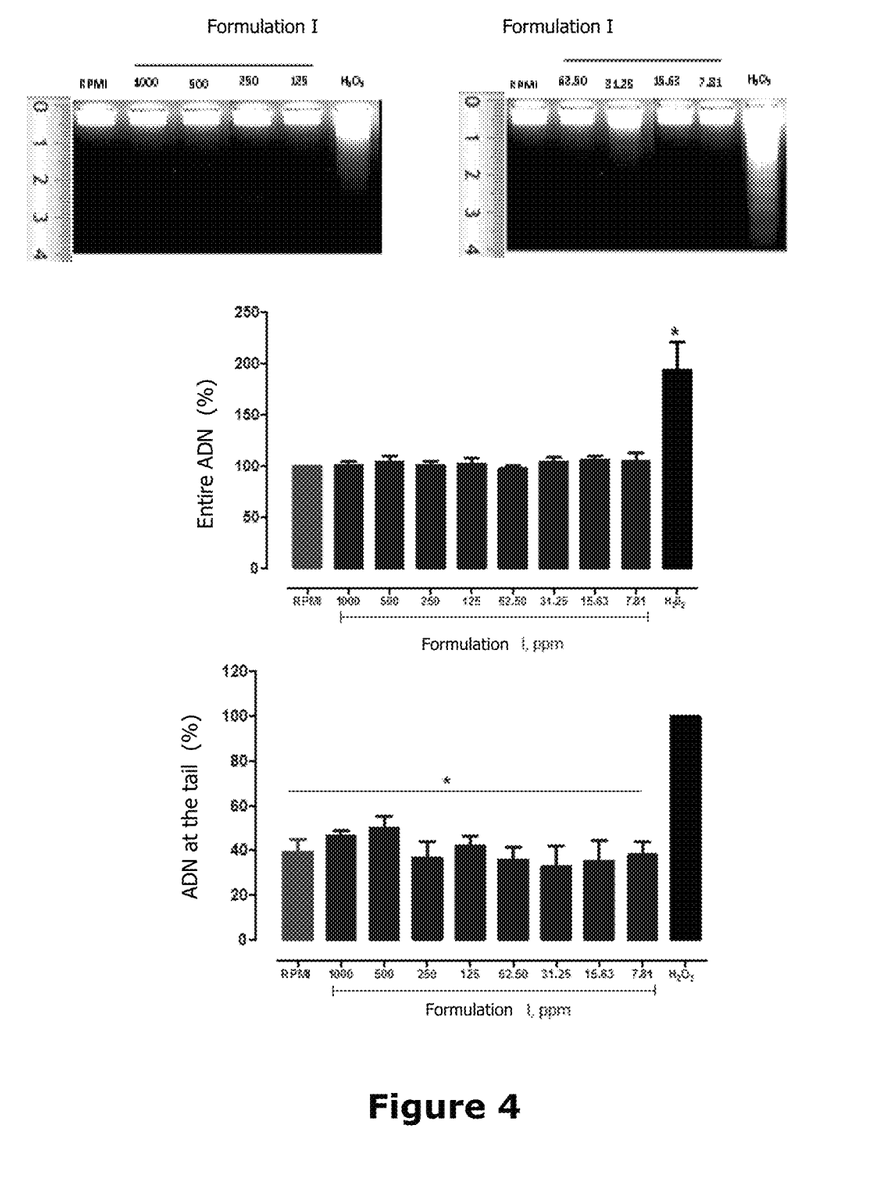
FIG. 4. Test genotoxicity of Formulation I applied at different concentrations in mononuclear cells (lymphocytes) above,—electrophoresis plates; in the middle,—percentage of integrated DNA (head) ($*p<0.05$ vs. White with RPMI); below,—the calculation based on the results of electrophoresis sample end ($*p<0.05$ vs. positive control with 0.1 mM $H_2O_2$).

Mononuclear cells and human peripheral blood lymphocytes were separated according to the same methodology described in Example 3. By using culture medium cell concentration was adjusted to 1×10$^6$ cells/mL. Cells obtained were seeded in Eppendorf vials at a density of 3×10$^4$ cells/mL and incubated at 37° C. and 5% $CO_2$ for 24 hours to stabilize. Subsequently vials were centrifuged at 1250 rpm for 5 min at 22° C. and supernatant was replaced with solutions of Formulation I to 7.81, 15.63, 31.25, 62.50, 125, 250, 500, and 1000 ppm (n=4 each). Blank test cells were resuspended in culture medium (n=8) and others with 0.1 mM hydrogen peroxide (positive control, n=8). Cells were incubated for 24 h to be later precipitated by centrifugation at 1200 rpm for 5 min and treated with 0.1 mL trypsin (0.25%) for 3 min at 37° C. and 5% $CO_2$. Cells were resuspended in 1 mL of RPMI 1640 medium and centrifuged again at 1200 rpm for 5 min, the supernatant was discarded and the cells were incubated with 1 mL of lysis solution (NaCl 2.5 M, $Na_2$EDTA 100 mM, Tris HCl 10 mM, and 1% Triton) at 4° C. for 24 h. After 24 h, vials were centrifuged at 1200 rpm at 4° C. The supernatant was discarded and cells were treated with 1 ml of neutralization buffer (0.4 M Tris pH 7.5) for 5 min at 4° C. Vials were centrifuged at 1200 rpm for 5 min at 4° C., cells were resuspended in 0.02 mL of loading buffer (bromophenol blue 0.25%, glycerol 50%, Tris-HCl 10 mM and 50 mM $Na_2$EDTA). Agarose gels were prepared by dissolving 1% in saline phosphate buffer (PBS) in a heating plate at 100° C. Once dissolved, and at 60° C., 0.01 mL Gelred (fluorescent dyeing DNA compound) was added. This mixture was placed in a horizontal electrophoresis chamber for 60 min. The lysed cells were loaded on agarose gels and incubated with the electrophoresis solution (1 mM $Na_2$EDTA and 300 mM NaOH at pH 13.5) for 20 min at 4° C. The electrophoretic running was performed at 25 V and 300 mA for 30 min at 4° C. Gels were removed from the electrophoresis chamber and revealed in a fluorescent signal analysis chamber. The generated images were acquired with a high resolution digital camera (FIG. 4, above) and analyzed with ImageQuant TL v8.1 software. The area of the comet head representing intact DNA was quantified by densitometric analysis and plotted as percentage versus the negative control (culture medium) (FIG. 4, in the middle). The tail of the comet representing the damaged DNA was measured in millimeters and represented as the percentage of the positive control ($H_2O_2$). Data were expressed as mean±mean standard deviation (FIG. 4, below). Data obtained were analyzed by analysis of variance (ANOVA) using in case of any difference a post-hoc Tukey test using GraphPad Prism v6.0 software, at $p<0.05$.

Results (FIG. 4) show that human peripheral blood mononuclear cells treated with various concentrations of Formulation I in RPMI 1640 culture medium supplemented with 10% FBS showed no damage in dsDNA (dsDNA). An apparent damage was not generated in the comet head (intact DNA) (FIG. 4, in the middle). In contrast, hydrogen peroxide (0.1 mM), known to exert genotoxic effects, shows the behavior in which a much more rapid dsDNA diffusion (FIG. 4, up and down) is detected, which is a genotoxicity indication, and due to this phenomenon the reading measuring area is much higher compared to Blank (FIG. 4, below). Behavior of samples treated with Formulation I was similar to the Blank, indicating that treatment with this for 24 h does not generate deleterious effects on mononuclear peripheral blood cell DNA (FIG. 4). In addition, the genotoxic effect induced by hydrogen peroxide (Azqueta A. and A. R. Collins in *Arch Toxicol*, 2013, 87: 949) was reproduced indicating that under experimental conditions, methodology developed is sensitive and trustable. Formulation I causes effects on cell growth without generating deleterious effects on human mononuclear cell DNA.

Example 5

The effect of different concentrations of Formulation I was evaluated on the human embryonic kidney (HEK-293) cell line and the Vero cell line (African green monkey kidney cells), using a microdilution assay with 3-(4,5-dimethyl-2-thiazolyl)-2,5-diphenyltetrazolium (MTT) (Mosmann T. in *J. Immunol Methods*, 1983, 65 (1-2.): 55). MTT method, based on reduction of 3-(4,5-dimethylthiazol-2-yl)-2,5-diphenyltetrazolium bromide, is an assay that reflects the metabolic function of cells. MTT is a yellow dye reduced to formazan (blue dye) by mitochondrial dehydrogenases, which are part of the respiratory chain of viable cells (Hwa et al., 2015). It is used in a quantitative colorimetric microdilution method applied for determination of survival and proliferative capacity of mammalian cells (Mosmann T. in *J. Immunol Methods*, 1983, 65 (1-2): 55). It is a suitable in vitro test for evaluating cell proliferation and cytotoxicity because it is simple, efficient, economical, reproducible, sensitive, safe, and effective as to viable cell population.

Figure 5:
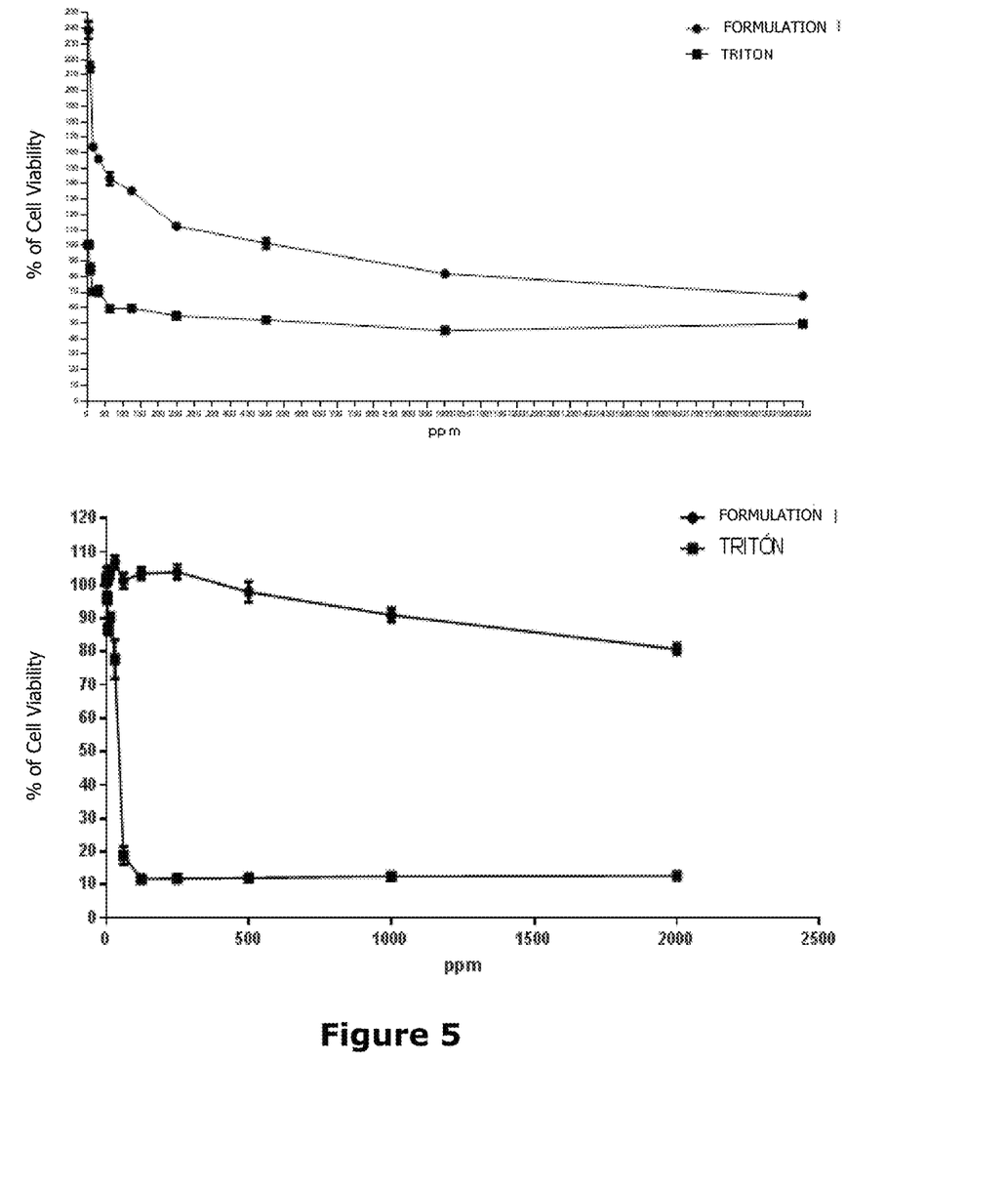
FIG. 5. Effect of different concentrations of Formulation I in viability of human embryonic kidney cell line HEK-293 cell culture (above) and African green monkey (Vero) kidney cell culture.

Dulbecco's modified Eagle Minimum Essential culture Medium/F12 (DMEM/F12) was used, supplemented with 10% fetal bovine serum (FBS) and 1 mL of a mixture of antibiotics (200,000 IU of penicillin and 0.5 g streptomycin). A trypsin solution (Difco) 0.25% was prepared. Serial dilutions from a 2000 ppm stock solution of Formulation I and Triton X-100 as solvent DMEM/F12 were prepared. 1 mL of each dilution was prepared to obtain concentrations of 1.95, 3.91, 7.81, 15.63, 31.25, 62.50, 125, 250, 500 and 1000 ppm. Cells of each cell cultures were grown using DMEM/F12 25 cm$^3$ culture plates until a confluent monolayer on the plate surface was obtained. Conditions used for cell culture were 37° C., humidified atmosphere with 5% $CO_2$. Confluent cell monolayer was lifted off 25 cm$^3$ plates using 0.25% trypsin. This was done as follows: DMEM/F12 medium was removed, then the monolayer washed 1 to 3 times with saline phosphate buffer 1× then added 0.5 mL of 0.25% trypsin, and the contents were incubated at 37° C. in humidified atmosphere with 5% $CO_2$ for 5 min. 3 ml of DMEM/F12 were added on the lifted cells, cells were resuspended with a 0.1-1 mL micropipette and placed in a 15 mL sterile conical tube, subsequently centrifuged at 1000 rpm for 5 min. DMEM/F12 was removed from conical tube. 3 ml of DMEM/F12 were added on cell pack, the cells resuspended, and a count was done in a Neubauer chamber. A cell suspension of 250,000 cells/mL was then prepared. 0.1 mL of the 250,000 cells/mL per well microplate cell suspension was added in all wells of a 96-well microplate, the microplate was incubated at 37° C. in humidified atmosphere with 5% $CO_2$ for 24 h. DMEM/F12 medium of each well was removed with vacuum, maintaining the monolayer at the bottom of each well, then 0.1 mL of each dilution prepared from Formulation I and Triton X-100 (1.95, 3.91, 7.81, 15.63, 31.25, 62.50, 125, 250, 500, 1000 and 2000 ppm) was added. Furthermore 8 wells were left with untreated cells used as control for cell viability (cell culture medium with no treatment—Blank), to which 0.1 mL of DMEM/F12 was added. Subsequently the microplate was incubated at 37° C. in humidified atmosphere with 5% $CO_2$ for 24 h. Then the DMEM/F12 medium was removed with the samples of Formulation I and Triton X-100, the wells were washed once with phosphate buffered saline. 0.02 mL was added to a MTT solution at 5 mg/mL and the content was incubated at 37° C. for 2 h, to conduct a complete reduction process of MTT to formazan by living cell mitochondrial dehydrogenases. Subsequently MTT solution was removed, retaining the formed formazan salts, then they added 0.1 mL of isopropyl alcohol and the absorbance at 540 nm was read in a Synergy HT microplate reader with GEN 5 embedded software. In the calculation of cell viability percentage detected absorbance in wells with cells proliferated in untreated culture medium were considered 100% of living cells. The Formulation I solutions were tested in quintuplicate and positive control solutions were tested in triplicate. The trial was conducted in three separate events. $LC_{50}$ data of Formulation I and Triton X-100 were estimated using the Graph Pad Prism version 6 Statistical Package, by Student's t test ($p<0.05$). Results of data analysis are expressed as the average±standard deviation (FIG. 5).

It was shown that for Formulation I at concentrations lower than 500 ppm, stimulation of proliferation and mitochondrial activity of HEK-293 and Vero cell lines was observed. HEK-293 line increase was 140% at 1.95 ppm and over 40% at 62.5 ppm concentration, while in the case of Vero cells only 10% compared to Blank. The results prove the effect of Formulation I to stimulate cell proliferation.

A dose-dependent cytotoxic effect was observed above 500 ppm since as Formulation I concentration was increased a decrease in cell viability (FIG. 5) was observed.

In both cell lines, the positive control (Triton X-100) showed a dose-depending effect, as a decrease in absorbance was observed by increasing the concentration of this substance, according to that expected as it is a cytotoxic compound, without any increase in viability (values greater than 100%), in any of the concentrations tested, but a decrease was detected in absorbance compared to Blank (with no treatment).

$LC_{50}$ for Formulation I and Triton X-100 were estimated with values of 2,417.00±65.77 and 764.10±21.93 ppm for HEK-293 cell line and 4,289.00±289.90 and 42.80±1.60 ppm for Vero cell line, respectively.

Results obtained prove that no cytotoxicity of Formulation I is observed at concentrations of 50-90 ppm range. At this dose cellular metabolism stimulation is observed. The observed phenomenon is similar to that described in Example 3 and demonstrates that Formulation I should be considered a growth and cellular metabolism factor-promoter.

Example 6

The effect of Formulation I was observed in healthy laboratory animals such as rodent and lagomorph models (Wistar rats and New Zealand rabbits) in the acute toxicity assay (single application, monitoring for 14 days) with high doses—higher than $LC_{50}$ of *A. salina* assay described in Example 2 (1000 and 1350 mg/kg) and subchronic toxicity test (daily application twice a day for ninety-day doses of 50, 70 and 90 mg/kg). The same procedures of adding placebo (purified water), measurement of weight and glycemia were performed in parallel in negative control animals of each animal species.

In all tests carried out on laboratory animals the treatment was orally administered in a weight-dependent measure, through orogastric cannula, after conventional feed consumption for rodents and lagomorphs (Commission of the European Communities in *Off. J. Eur. Comm* (L 383 A), 1992, 35: 110), respectively.

Animals were kept in individual cages and were observed continuously for the first 24 h after administration of Formulation I, continuing the observation and intermediate veterinary care needed for each test period being recorded in a logbook for any animal response. Body weight was determined and recorded at the beginning and end of the experiment. Also in case of rabbits, clinical laboratory tests were performed before and after each test: blood biometry, blood chemistry and activity of transaminase enzymes: aspartate aminotransferase (AST), alanine aminotransferase (TGP) and transpeptidase gamma glutamyl transaminase (GGT). In rats, these parameters were determined only at the end of testing to prevent blood loss. Finally, we proceeded with the euthanasia step to animals applying a series of anesthetics and potassium chloride (KCl). Subsequently, an organ and fundamental tissue macroscopic examination and necropsy was conducted, primarily including heart, kidney, spleen, pancreas, lung, liver, ovaries and testicles, according to each case. Samples taken were sent to carry out a histopathological study.

Figure 6:
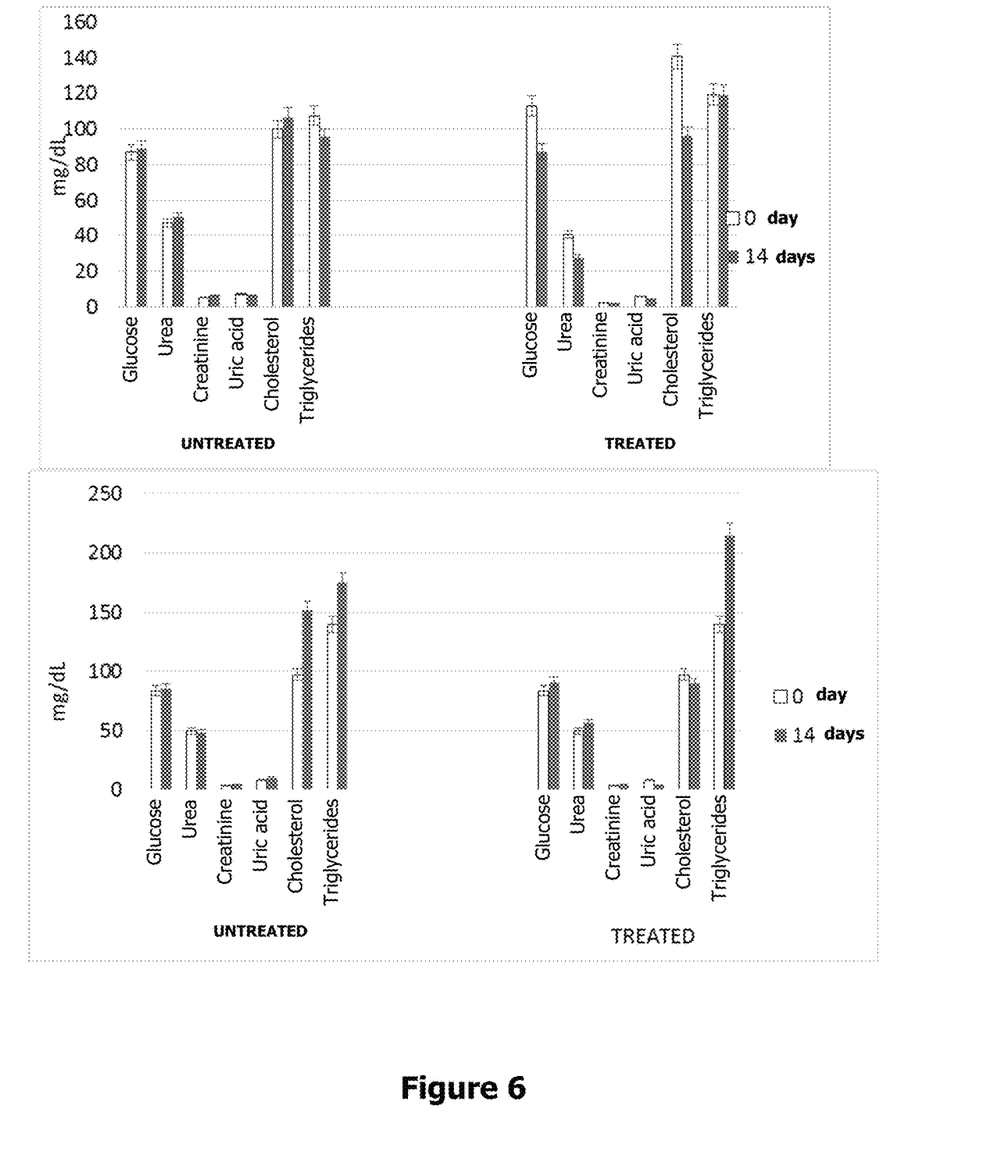
FIG. 6. Graphical representation of the values for blood chemistry parameters in animals with and without treatment with Formulation I: above—male rabbits; below, —male rats, prior to application of the single dose and after 14 days application of 1000 mg/Kg.

Maximum dose tested in the acute toxicity assay was 1350 mg/kg because the maximum volume applied by orogastric cannula is 1 or 3 ml for rodents and lagomorphs, respectively, and the use of higher doses led to obtaining a more viscous solution having difficulty passing the orogastric cannula. With the tested concentrations any death of laboratory animals was not observed, thus the LD50 value was not determined. Regarding the present invention, it was shown that most of the evaluated parameters, including weight and activity of liver enzymes and blood biometry, showed no significant difference before and after treatment and compared with Blank (no treatment). However, in treated animals a decrease of glucose levels, a decrease of uric acid and cholesterol (FIG. 6) was appreciated. Because these parameters are related to metabolic syndrome, gout and diabetes, the test results indicate that the application of a single, Formulation I high dose leads to diminution of metabolite levels above and confirms the effect of use of this treatment for mentioned pathologies.

The same trend was observed in the case of the results of sub-chronic toxicity study. Decreased levels of glucose, cholesterol, uric acid, creatinine and liver enzymes was observed with the application of Formulation I at different doses. However, the statistically proven difference was only obtained with glucose control while changing other parameters is characterized by large standard deviation associated with individuality of subject in animals under study. Increased body weight in case of treated animals was lower than in the control. Furthermore, a repeatedly decrease in liver enzyme activity was observed which can be regarded as evidence of an effect of Formulation I to improve liver activity. The characteristic observation while performing autopsies was that animals treated with Formulation I in macroscopic evaluation faced significant muscle development and little development of body fat, in the same way they showed no hepatic steatosis. All this even though held for 90 days with very little movement inside the cages, i.e. without exercise and normal food intake according to weight and age. These results also confirm that the application of Formulation I allows weight control mediated by a decreased amount of adipose tissue, glucose control and occasionally other characteristics of blood chemistry, without altering blood biometry and liver function in healthy mammals.

Example 7

In addition, the test in rats and rabbits with alloxan-induced diabetes was performed. In this test, as well as in the sub-chronic toxicity study, treatments were applied to three doses of Formulation I (50, 70 and 90 mg/kg). 5 groups of animals with treatments (insulin plus Formulation I at three mentioned doses, Formulation I at 70 mg/kg and insulin alone) were examined. Insulin glargine was administered subcutaneously at a dose of 0.7 U/kg in a single morning administration every 24 h.

Comparison of analysis results of blood chemistry in diabetes-induced rabbits at the beginning and end of the assay, found that even under treatment, glycemia are manifested at high level. An increase of urea and creatinine was observed, confirming kidney damage. However, in the case of rabbits treated with Formulation I, a decrease of levels of uric acid and cholesterol was observed Blood biometry results of rabbit blood before and after 21 days of application of treatments showed decrease in parameters related to the presence of monocytes and platelets and hemoglobin as a result of induced diabetes in animals. Monocytosis is a condition where an increase in the presence of a type of blank blood cells known as monocytes is present. Monocytes are formed in the bone marrow and play an important role in the normal functioning of the immune system. Platelets are involved in blood clotting, helping to stop bleeding in case of injury. Observed changes indicate that during treatment of alloxan-induced diabetes, blood disorders or bone marrow were formed.

Figure 7:
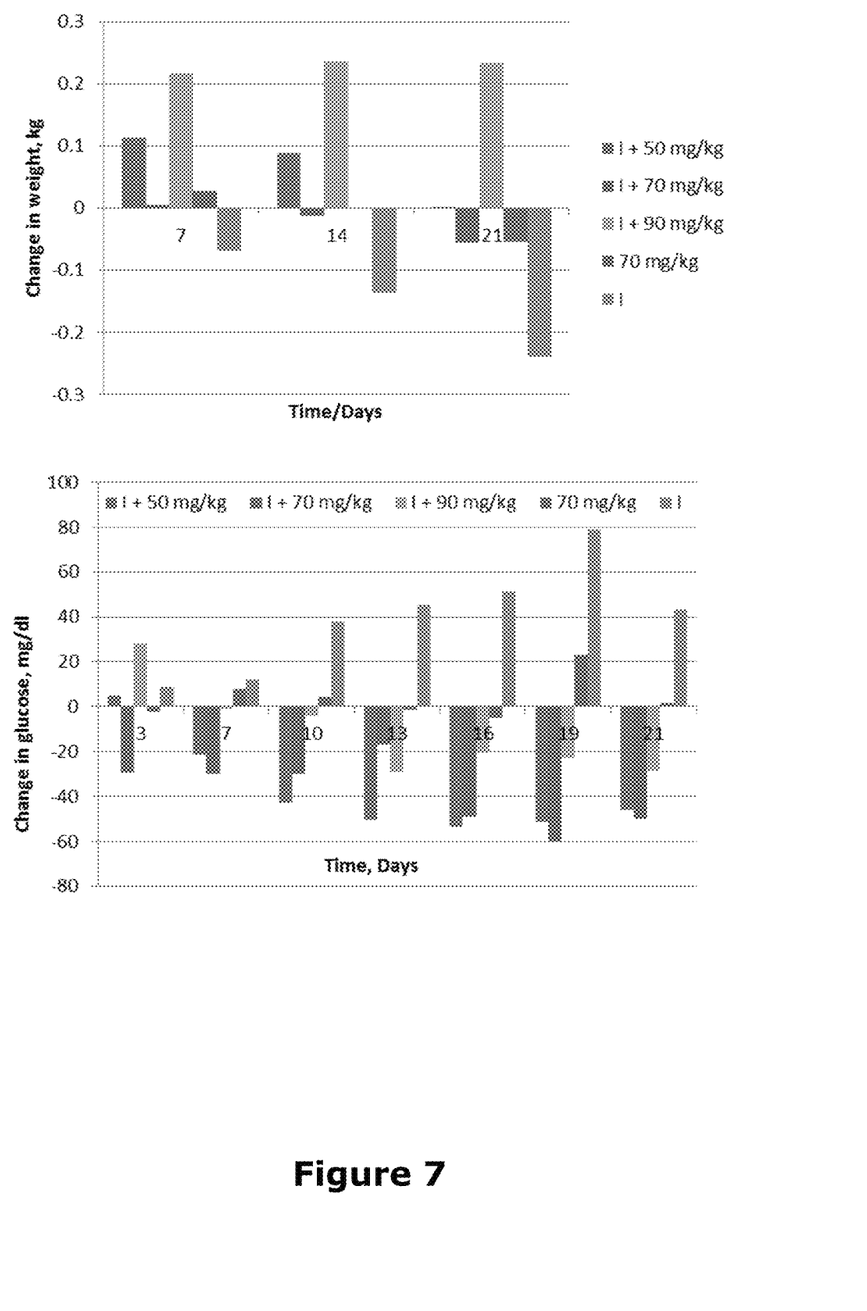
FIG. 7. Weight change dynamics (top) and glucose concentration (capillary glycemia) (below) in different groups of lagomorph animals subjected to treatment: I—insulin and 50, 70, 90 mg/kg—in Formulation I dose.

During clinical monitoring, several rabbit specimens showed weight loss associated with alterations in food intake and water (periods of anorexia with polydipsia), expected clinical data in any diabetic body. Some rabbits of the group of animals treated with 90 mg/kg Formulation I and insulin, a weight loss was not detected as all other animals, even having evidence of weight gain, which shows that Formulation I shows organic protection. FIG. 7 (above) shows the trend of weight change in different groups of animals tested in the study. It is appreciated that the application of Formulation I leads to less weight loss. For groups treated with Formulation I and insulin, the greater weight gain is observed in the group with application of 90 mg/kg. This shows that the effect is dose-dependent.

Likewise, all specimens handled with Insulin and Formulation I corroborated that it shows a hypoglycemic effect as in Examples 5 and 6. FIG. 7 (below) shows average values of capillary glucose levels in different days of treatment application. It is seen that the effect varies with different doses and is greater than 50 and 70 mg/kg compared to 90 mg/kg.

Figure 8:
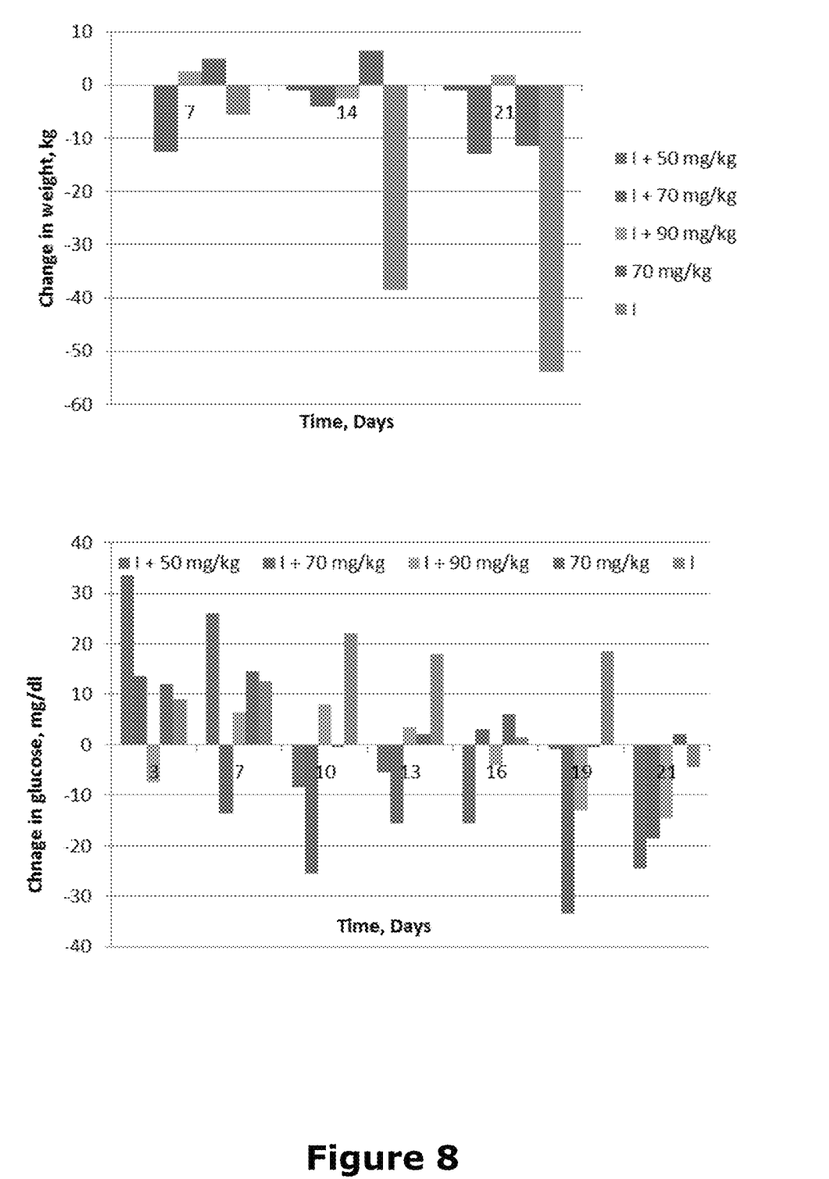
FIG. 8. Weight change dynamics (top) and glucose concentration (capillary glycemia) (below) in different groups of rodents subjected to treatment with: I—insulin and 50, 70, 90 mg/kg—in formulation I dose.

FIG. 8 (above) shows average values of weight change per group of rats with induced diabetes. In the case of group animals treated with pure insulin (I) a tendency of weight loss decrease is much more visible when compared to the other groups tested with study treatment. FIG. 8 (below) presents the average values of change of the glucose concentration (capillary glucose). For rats treated only with insulin an increase in the tendency for capillary glucose is seen up to 19 days of treatment. It is appreciated that in this period increased glucose is controlled more efficiently by only applying Formulation I to 70 mg/kg. The largest decrease of glucose levels in type 1 diabetic animals is observed for 70 mg/kg doses.

In clinical monitoring of rats with induced diabetes (type 1 diabetes), specimens of the groups treated only with insulin or Formulation I showed changes in feed intake and water (periods of anorexia with polydipsia), as in rabbits, these clinical data in any diabetic body are expected. However, the groups subject to treatment with Formulation I plus insulin did not show these clinical data so markedly, i.e. the application of treatments helped improve the quality of life of animals and joint management with insulin could improve clinical status of animals with diabetes showing the effect claimed in the present invention.

Glucose levels in rats treated with 50 and 70 mg/kg of Formulation I plus insulin (Glargine) tended to normalization (FIG. 8, below). With regard to monitoring the group treated with 90 mg/kg and Insulin (Glargine), although the glycemia tended not to normalize in this short period of exposure, very similar data to those obtained in the lagomorph species with the same doses of treatment were observed (FIG. 7). In both cases the results demonstrate that Formulation I shows organic protection from mammals with diabetes.

Comparison of blood chemistry analysis results among different groups of rats in the test prove that still under treatment, glycemias is manifested at high levels and high values of urea and creatinine were observed, confirming damage to kidneys. Blood biometry results show no significant differences between different groups tested.

Figure 9:
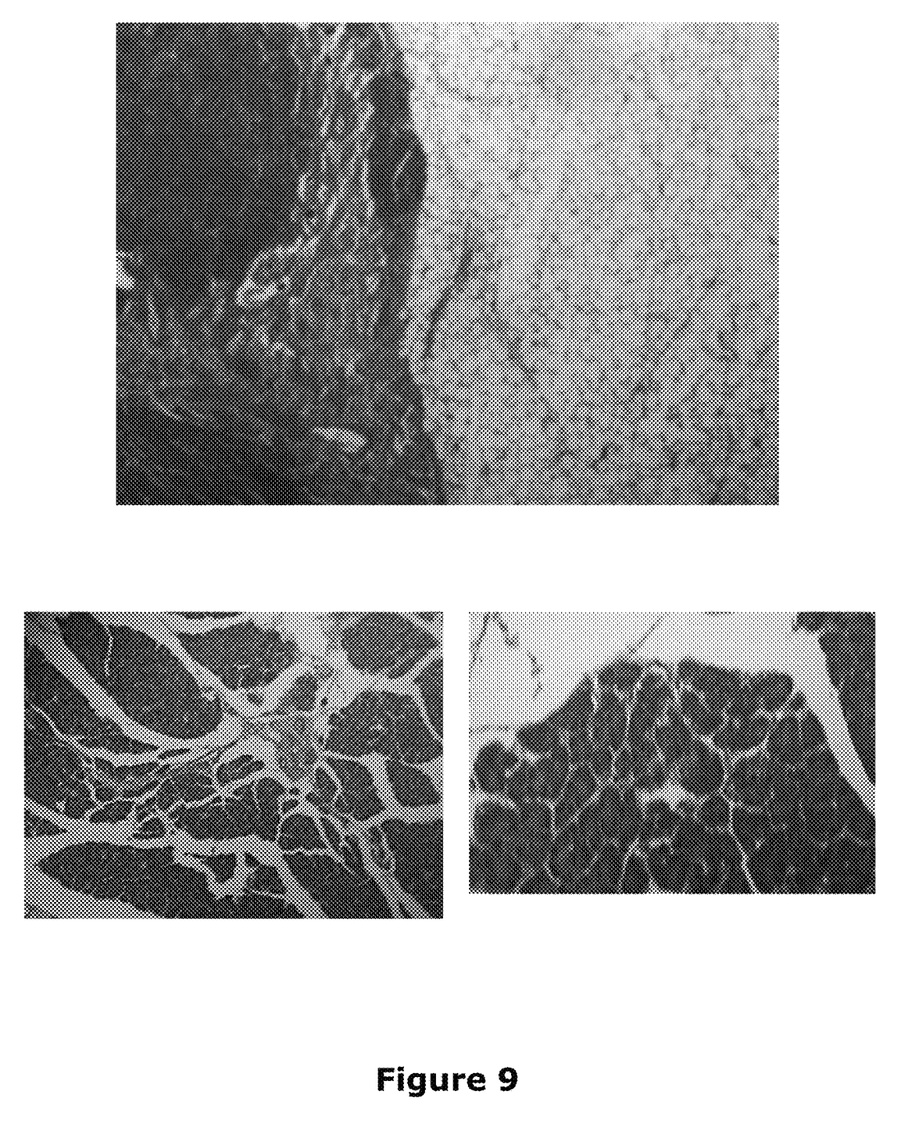
Figure 10:
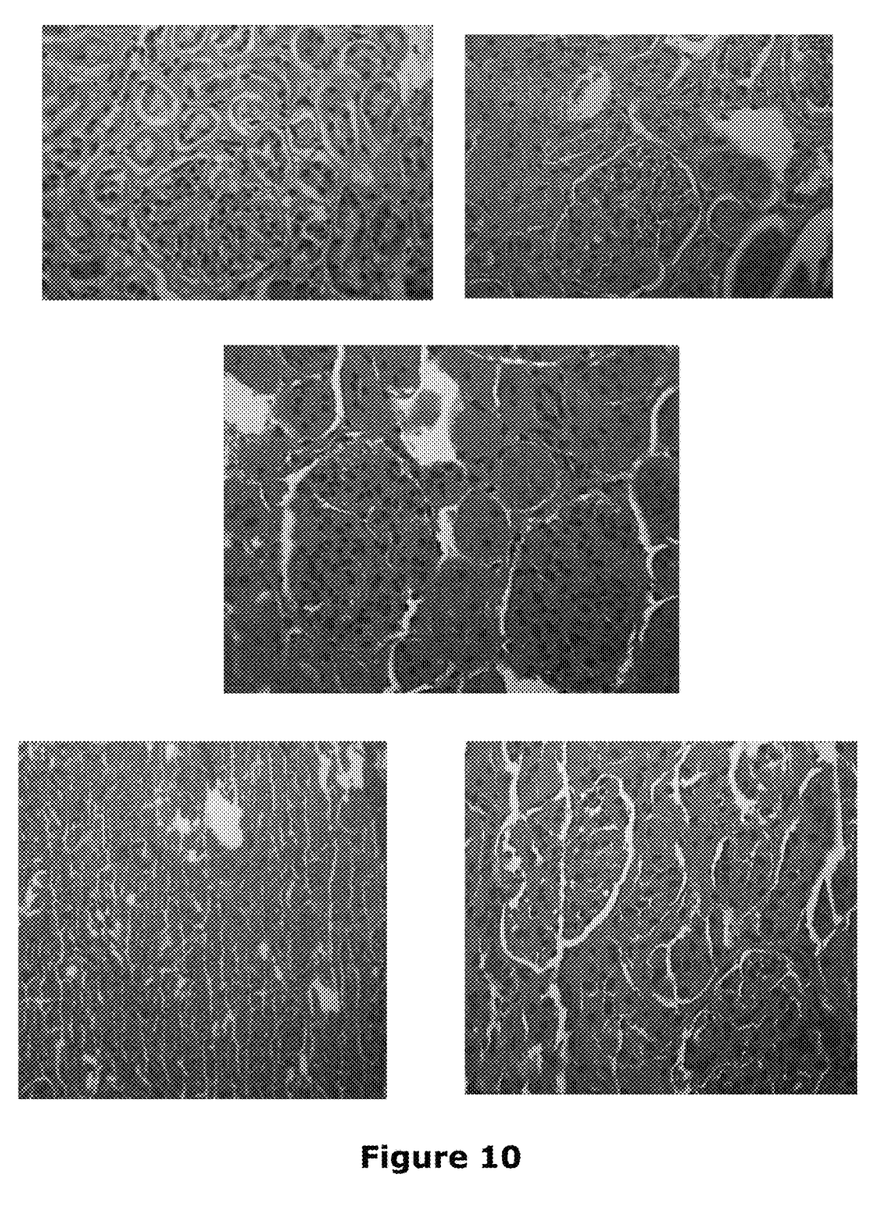

In the macroscopic study after rabbit and rat autopsy with type I diabetes, groups treated with only supplement or insulin were observed to present the most severe pancreatic alterations, having been confirmed in the histopathological sections (FIG. 9). Thus, alloxan as diabetes inducer, affects this organ and alteration was expected in all animals. However, animals treated with Formulation I and insulin, showed no macroscopically detectable alterations. It is known the effect of resveratrol to increase the sensitivity of insulin receptors (Chachay V. S. et al in *Br J Clin Pharmacol*, 2011, 72 (1): 27). However, in the description of the present invention Formulation I also demonstrates a further cytoprotective effect on animal organs and a recovery effect of damaged tissues when acting in presence of insulin.

According to histopathology results performed with samples of animals induced with diabetes, kidney damage (result consistent with blood chemistry analysis) is observed. However, in the specimens of groups treated with insulin and Formulation I, less kidney damage was observed than in specimens treated only with Formulation I or insulin alone. Together with the results of weight control and capillary glycemia, these results provide evidence that during the trial period (21 days) treatment applied with Formulation I along with insulin leads to protection of organs such as kidney and pancreas against changes caused by diabetes.

The examples shown herein confirm the ability of Formulation I to protect the organs of type 1 diabetes mammals against deterioration when applied with insulin. Furthermore, the ability to control blood sugar is noticed, which is enhanced in the presence of insulin, and the effect is seen to maintain weight gain, lowering cholesterol and uric acid.

Example 8

A 48-year man presented chest discomfort and subsequently diagnosed to have metabolic syndrome. Physical examination showed an obese person with a body weight of 87 kg, height 170 cm, with a BMI of 32 kg/m$^2$. Blood pressure (BP) was 160/110 mm Hg, fasting plasma glucose (GA) was 150 mg/dL, triglycerides (Tg) of 215 mg/dL, total cholesterol (TC) 320 mg/dL, LDL-C 212 mg/dL, HDL-C 37 mg/dL, and HbA1c of 8.46%. The patient was subject to treatment with Formulation I as described in Example 2, three times a day after each food intake over the next 6 months. The form of application of Formulation I was prepared in a glass of water or juice suspension. Periodic evaluations were carried out to estimate affinity therapy and avoid any side effects. After this period of treatment with Formulation I, we proceeded to perform biochemical studies. Detected values were: GA 115 mg/dL, HbA1c 6.69%, TC 235 mg/dL, LDL-C 123.7 mg/dL, HDL-C 40 mg/dL, Tg 119 mg/dL and his weight dropped 74 kg. The level of 11-dehydro thromboxane B2 and platelet aggregation were reduced respectively by 75% and 90% compared to baseline. The response to therapy was 100%. With this procedure, the patient had a considerable modification of risk factors for metabolic syndrome.

Finally it must be understood that the use of glycine, cysteine, arginine and resveratrol to treat and prevent metabolic syndrome, diabetes, obesity, and as anti-aging treatment, is not limited to Formulation I and embodiments described above, and those skilled in the art will be trained by the teachings set forth herein to make changes in the treatment composition of the present invention, the scope will be established solely by the claims.

REFERENCES

Alcaín, F. J., Villalba, J. M. (2009). "Sirtuin activators". *Expert Opin Ther Pat.*, 19(4): 403-414. doi:10.1517/13543770902762893. PMID 19441923.

Azqueta, A., Collins A. R. (2013). "The essential comet assay: a comprehensive guide to measuring DNA damage and repair". *Archives of toxicology*, 87: 949-968.

Baur, J. A. et al., (2006). "Resveratrol improves health and survival of mice on a high calorie diet". *Nature*, 444 (7117): 337-342.

Beher, D., Wu, J., Cumine, S., Kim, K. W., Lu, S. C., Atangan, L., Wang, M. (2009). "Resveratrol is not a direct activator of SIRT1 enzyme activity". *Chem Biol Drug Des.*, 74 (6): 619-624. doi:10.1111/j.1747-0285.2009.00901.x.PMID 19843076.

Chachay, V. S, Kirkpatrick, C. M. J., Hickman, I. J., Ferguson, M., Prins, J. B., Martin, J. M. (2011). "Resveratrol—pills to replace a healthy diet?" *Br J Clin Pharmacol.* 72(1): 27-38

Commission of the European Communities. (1992). "Annex to Commission Directive 92/69/EEC of 31 Jul. 1992 adapting to technical progress for the seventeenth time Council Directive 67/548/EEC on the approximation of laws, regulations and administrative provisions relating to the classification, packaging and labelling of dangerous substances. B.1 Acute toxicity (oral)". *Off. J. Eur. Comm.* (L 383 A) 35: 110-112.

Do, G. M. et al., (2008). "Long-term effects of resveratrol supplementation on suppression of atherogenic lesion formation and cholesterol synthesis in apo E-deficient mice". *Biochem. Biophys. Res. Commun.*, 374(1): 55-59.

Duffy, S. J., Vita, J. A. (2003). "Effects of phenolics on vascular endothelial function". *Current Opinion in Lipidology*, 14 (1): 21-27. doi:10.1097/01.mol.0000052857.26236.f2, PMID 12544657.

Eckel, R. H., Grundy, S. M., Zimmet, P. Z. (2005). "The metabolic syndrome". *Lancet,* 365: 1415-1428.

Environmental Protection Agency (2002). "Methods for measuring the acute toxicity of effluents and receiving waters to freshwater and marine organisms". Fifth Edition. U.S. Environmental Protection Agency Office of Water (4303T) 1200 Pennsylvania Avenue, NW Washington, D.C. 20460 PP. 178-184.

Fremont, L. (2000). "Biological effects of resveratrol". *Life Sci.,* 66: 663-673.

Ganem Baez, F. A., Martin Gonzalez, O. (2000). "Lectina concanavalina A: obtención y purificación". *Universo Diagnóstico.* 1(1):1-41.

Ghosh, H. S., McBurney, M., Robbins, P. D., McBurney, R. (2010). "SIRT1 negatively regulates the mammalian target of rapamycin". *PLoS ONE* 5 (2): e9199. Bibcode: 2010PLoSO . . . 5.9199G. doi:10.1371/journal.pone.0009199.PMC 2821410.PMID 20169165.

Gokaraju G. R., Gokaraju, R. R., Golakoti, V. K. R. R., Bhupathiraju, T., Sengupta, K., Alluri, K., Raju, V. K. (2016). Composition from *Sphaeranthus indicus* and *Garcinia mangostana* for the control of metabolic syndrome. Patent US 2016/9,241,964, Jan. 26, 2016.

Gualdrón, R., López, S., Sanabria, A. (1997). Estudio fitoquímico preliminar y letalidad sobre *Artemia salina* de plantas colombianas. *Rev. Col. Quím. Farm.* 26:15-19.

Jiang, W. J. (2008). "Sirtuins: novel targets for metabolic disease in drug development". *Biochem. Biophys. Res. Commun.* 373(3): 341-344.

Lagouge, M., Argmann, C., Gerhart-Hines, Z., Meziane, H., Lerin, C., Daussin, F., Messadeq, N., Milne, J., Lambert, P., Elliott, P., Geny, B., Laakso, M., Puigserver, P., Auwerx, J. (2006). "Resveratrol improves mitochondrial function and protects against metabolic disease by activating SIRT1 and PGC-1alpha". *Cell* 127 (6): 1109-1122. doi: 10.1016/j.cell.2006.11.013. PMID 17112576.

Lodder, R. A., Cassis L. A. (2016). D-tagatose-based compositions and methods for preventing and treating atherosclerosis, metabolic syndrome, and symptoms thereof. Patent US 2015/9,060,962, Jun. 23, 2015.

Martí-Centelles, R., Falomir, E., Murga, J., Carda, M., Marco, J. A. (2015). Inhibitory effect of cytotoxic stilbenes related to resveratrol on the expression of the VEGF, hTERT and c-Myc genes. *Eur J Med Chem.* 103: 488-496.

Michael, A. S., Thompson, C. G., Abramovitz, M. (1956). *Artemia salina* as test organims for a bioassay. *Science.* 123: 464.

Mosmann, T. (1983). Rapid calorimetric assay for cellular growth and survival: application to proliferation and cytotoxicity assays. *J Immunol Methods.* 65(1-2): 55-63.

Olas, B., Wachowicz, B. (2005). "Resveratrol, a phenolic antioxidant with effects on blood platelet functions". *Platelets* 16 (5): 251-260.

Prossnitz, E. R., Barton, M. (2014). "Estrogen biology: New insights into GPER function and clinical opportunities". *Molecular and Cellular Endocrinology.* 389 (1-2): 71-83. doi: 10.1016/j.mce.2014.02.002. ISSN 0303-7207.

Romero, T. (2016). Methods and materials for reducing multiple risk factors associated with the metabolic syndrome. Patent US 2016/9,278,104, Mar. 8, 2016.

Vanhaecke, P., Persoone, G., Claus, C., Sorgeloos, P. (1981). "Proposal for a short-term toxicity test with *Artemia nauplii*". *Ecotoxicol Environ Saf.* 5: 382-387.

Varfolomeev, S. D., Gurevich, K. G. (2001). Enzyme active sites: bioinformatics, architecture, and mechanisms of action. *Russian Chemical Bulletin.* 50 (10): 1709-1717.

Wang, L., Waltenberger, B., Pferschy-Wenzig, E. M., Blunder, M., Liu, X., Malainer, C., Blazevic, T., Schwaiger, S., Rollinger, J. M., Heiss, E. H., Schuster, D., Kopp, B., Bauer, R., Stuppner, H., Dirsch, V. M., Atanasov, A. G. (2014). "Natural product agonists of peroxisome proliferator-activated receptor gamma (PPARγ): a review". *Biochem Pharmacol* 92 (1): 73-89. doi: 10.1016/j.bcp.2014.07.018. PMC 4212005. PMID 25083916.

Wu, G. A. B., Meininger, C. J., Knabe, D. A., Baze, F. W. A., Rhoads, J. M. (2000) "Arginine nutrition in development, health and disease". *Current Opinion in Clinical Nutrition & Metabolic Care.* 3 (1): 59-66.

What is claimed is:

1. A method for treating or preventing a metabolic syndrome, the method consisting of:
administering to a patient a composition consisting of 3,000-7,000 mg glycine, 300-5,000 mg arginine, 200-2,500 mg cysteine, and 100-2,500 mg resveratrol.

2. The method of claim 1, wherein the composition is an aqueous suspension, tablet, or polymer capsule.

3. The method of claim 1, wherein the administering of the composition further reduces total cholesterol, low density lipoproteins, and triglyceride levels in blood of the patient.

4. The method of claim 1, wherein the administering of the composition further reduces uric acid concentration in blood of the patient.

5. The method of claim 1, wherein the administering of the composition further decreases plaque volume in arteries of the patient.

6. The method of claim 1, wherein the administering of the composition further reduces body fat of the patient.

7. The method of claim 1, wherein the administering of the composition further reduces high blood glucose concentration(s) of the patient.

8. The method of claim 1, wherein administering of the composition further reduces progression severity of the metabolic syndrome of the patient.

9. The method of claim 1, wherein the administering of the composition further stimulates cell proliferation in organs of the patient damaged by the metabolic syndrome.

\* \* \* \* \*